US00PP31939P2

(12) United States Plant Patent
Malinowski et al.

(10) Patent No.: US PP31,939 P2
(45) Date of Patent: Jul. 7, 2020

(54) ***HIBISCUS* PLANT NAMED '15734-1 GR'**

(50) Latin Name: ***Hibiscus* hybrid (L.)**
Varietal Denomination: 15734-1 GR

(71) Applicant: The Texas A&M University System, College Station, TX (US)

(72) Inventors: Dariusz P. Malinowski, Vernon, TX (US); William E. Pinchak, Vernon, TX (US); R. Steve Brown, Vernon, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 16/501,691

(22) Filed: May 22, 2019

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 6/608; A01H 5/02
See application file for complete search history.

(56) References Cited

U.S. PATENT DOCUMENTS

PP11,853 P2 5/2001 Fleming et al.
PP11,854 P2 5/2001 Fleming et al.

OTHER PUBLICATIONS

U.S. Appl. No. 16/501,884, filed Jun. 25, 2019, Malinowski et al.
U.S. Appl. No. 16/501,696, filed May 22, 2019, Malinowski et al.
U.S. Appl. No. 16/501,698, filed May 22, 2019, Malinowski et al.
U.S. Appl. No. 16/501,694, filed May 22, 2019, Malinowski et al.
U.S. Appl. No. 16/501,693, filed May 22, 2019, Malinowski et al.
U.S. Appl. No. 16/501,695, filed May 22, 2019, Malinowski et al.
U.S. Appl. No. 16/501,692, filed May 22, 2019, Malinowski et al.
U.S. Appl. No. 16/501,697, filed May 22, 2019, Malinowski et al.

*Primary Examiner* — Keith O. Robinson
(74) *Attorney, Agent, or Firm* — Dentons US LLP

(57) ABSTRACT

'15734-1 GR' is a new and distinct hardy herbaceous *Hibiscus* hybrid with novel characteristics that include upright branched stems, numerous, outward-facing, reddish purple flowers that have a center eye that is between dark red and deep purplish red, a prolonged blooming season, and hastate, trilobed leaves.

4 Drawing Sheets

Latin name of the genus and species of the plant claimed: *Hibiscus* hybrid (L.).

Cultivar denomination: '15734-1 GR'.

BACKGROUND OF THE INVENTION

The invention relates to the new and distinct *hibiscus* plant '15734-1 GR'. '15734-1 GR' was generated from a cross performed on Jul. 12, 2014 near Vernon, Tex. between '12078-5' (pod parent, unpatented) and '14188-2W' (pollen parent, unpatented). The pedigrees of each parent reflect a complex mixture of *hibiscus* species that include, for example, *H. mocheutos, H. coccineus, H. militaris*, or *H. dasycalyx*. The seed from this cross was harvested on Aug. 30, 2014 and the '15734-1 GR' seedling was selected in the summer of 2015. '15734-1 GR' was first asexually propagated near Vernon, Tex. in 2016 by stem tip cuttings. The resulting as well as subsequent asexually propagated plants have been stable and true to type throughout successive generations.

SUMMARY OF THE INVENTION

'15734-1 GR' differs from its parents and all other known hardy herbaceous *hibiscus* plants. The following are the most outstanding and distinguishing characteristics of '15734-1 GR': (1) it is a hardy perennial with dense branching and a compact growth habit; (2) it blooms profusely over a prolonged season; and (3) its flowers exhibit a reddish purple (RHS 72C) background and a center eye that is between dark red (RHS 59A) and deep purplish red (RHS 59B).

'15734-1 GR' plants can be readily and unambiguously distinguished from those of its parents. '15734-1 GR' plants exhibit strong reddish purple (RHS 72C) flowers that have an average diameter of 20 cm and hastate, trilobed leaves. Whereas, '12078-5' plants (pod parent) exhibit light purplish blue (RHS 95D) to very pale purplish blue (RHS 97C) flowers that have an average diameter of 10 cm and lobed leaves; and '14188-2W' plants (pollen parent) exhibit light purple (RHS 84C) flowers that have an average diameter of 18 cm and lobed leaves.

'Plum Crazy' (U.S. Pat. No. 11,854), which is within the pedigree of '15734-1 GR', is the *hibiscus* plant that exhibits flowers that are colored most similarly to those of '15734-1 GR'. Nonetheless, plants of '15734-1 GR' and 'Plum Crazy' can also be readily and unambiguously distinguished from one another at least based upon flower shape, petal shape, flowering time, flowering amount, and growth habit. The petals of '15734-1 GR' are not cupped and only slightly overlapping; whereas, the petals of 'Plum Crazy' are cupped and very overlapping. Also, '15734-1 GR' plants exhibit a more compact growth habit, earlier flowering, and more profuse flowering than 'Plum Crazy' plants. '15734-1 GR' plants can also be readily and unambiguously distinguished from 'Fantasia' plants (U.S. Pat. No. 11,853) at least based upon flower shape, flower color, and growth habit. The petals of '15734-1 GR' are less overlapping than the cupped petals of 'Fantasia', and plants of '15734-1 GR' exhibit a more compact growth habit than plants of 'Fantasia'.

BRIEF DESCRIPTION OF THE DRAWINGS

'15734-1 GR' is illustrated by the accompanying photographs, which show the plant's form, foliage, flowers, and leaves. The colors shown are as true as can be reasonably obtained by conventional photographic procedures.

DETAILED BOTANICAL DESCRIPTION

Figure 1:
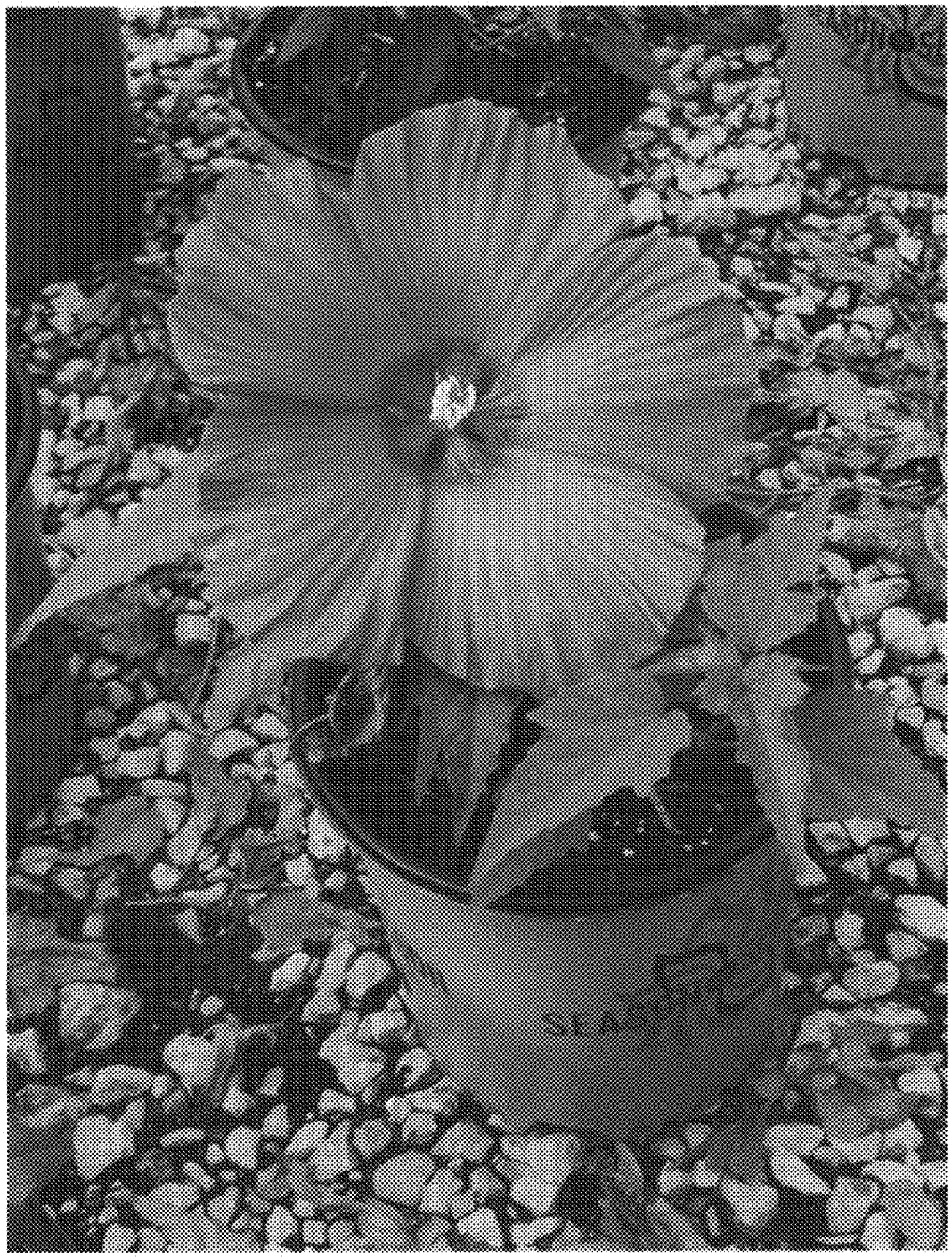
FIG. 1—Shows a 6-week-old '15734-1 GR' plant in a container.
Figure 2:
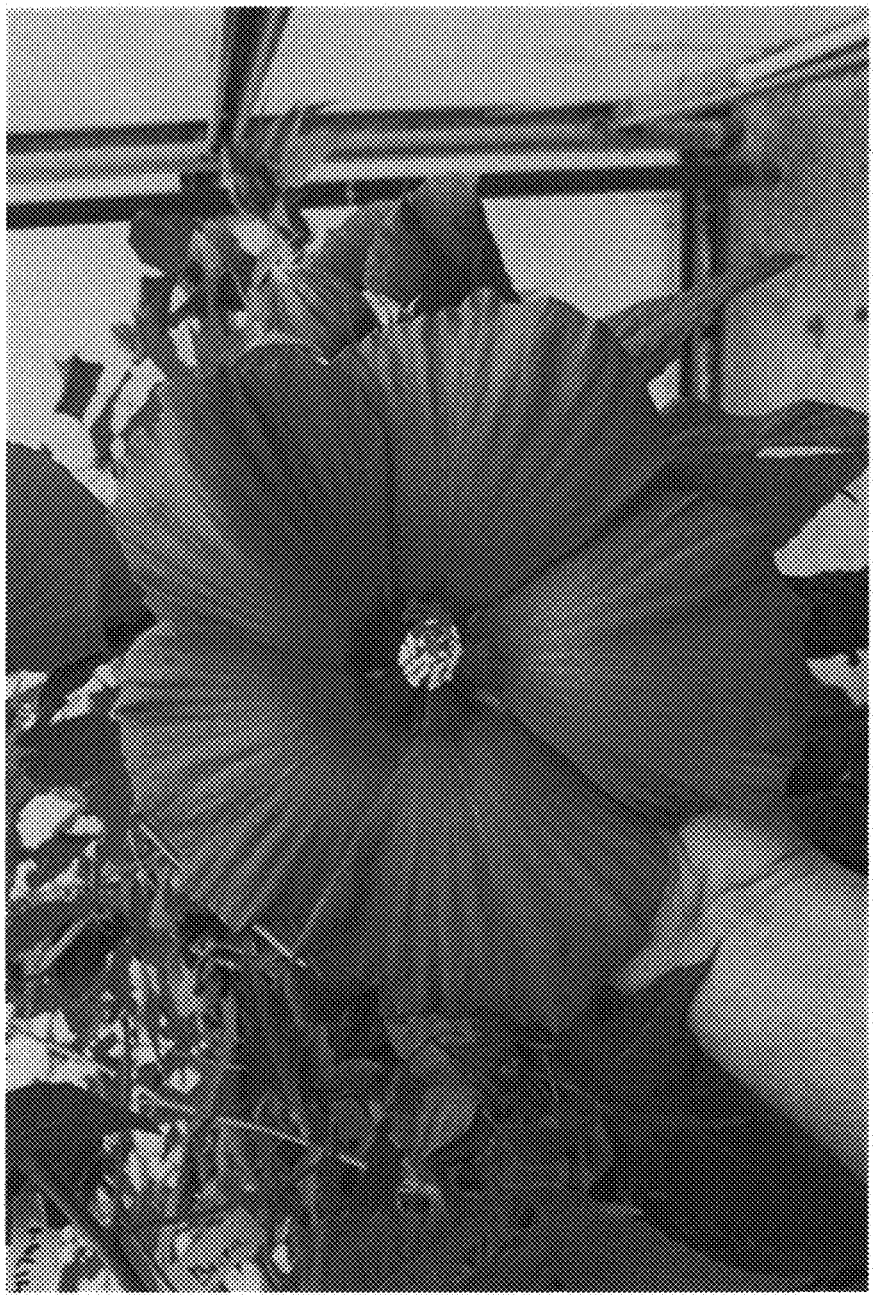
FIG. 2—Shows a '15734-1 GR' flower as seen looking directly at the adaxial surface of the petals on a 2-year-old plant.
Figure 3:
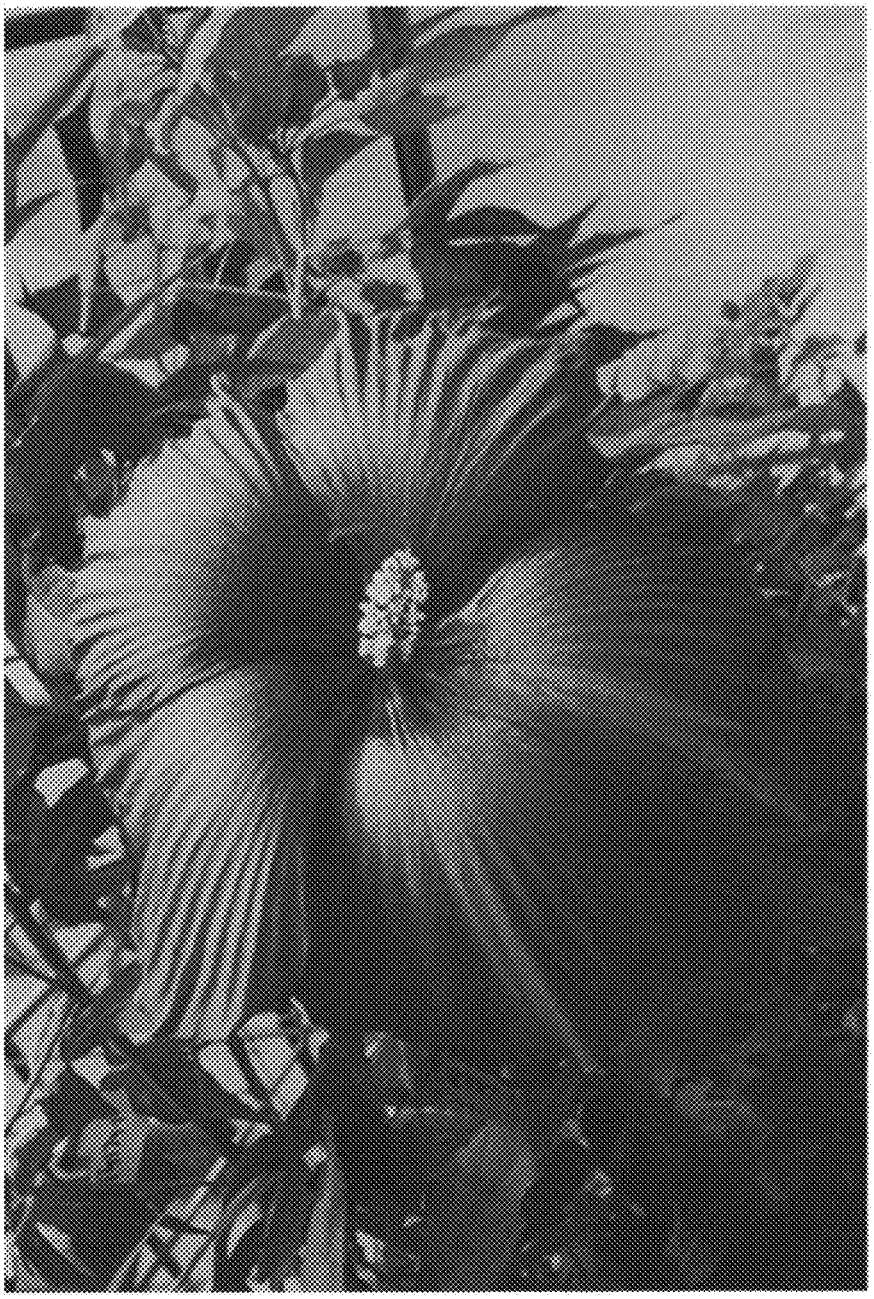
FIG. 3—Shows a '15734-1 GR' flower as seen looking slightly askew from the adaxial surface of the petals on a 2-year-old plant.
Figure 4:
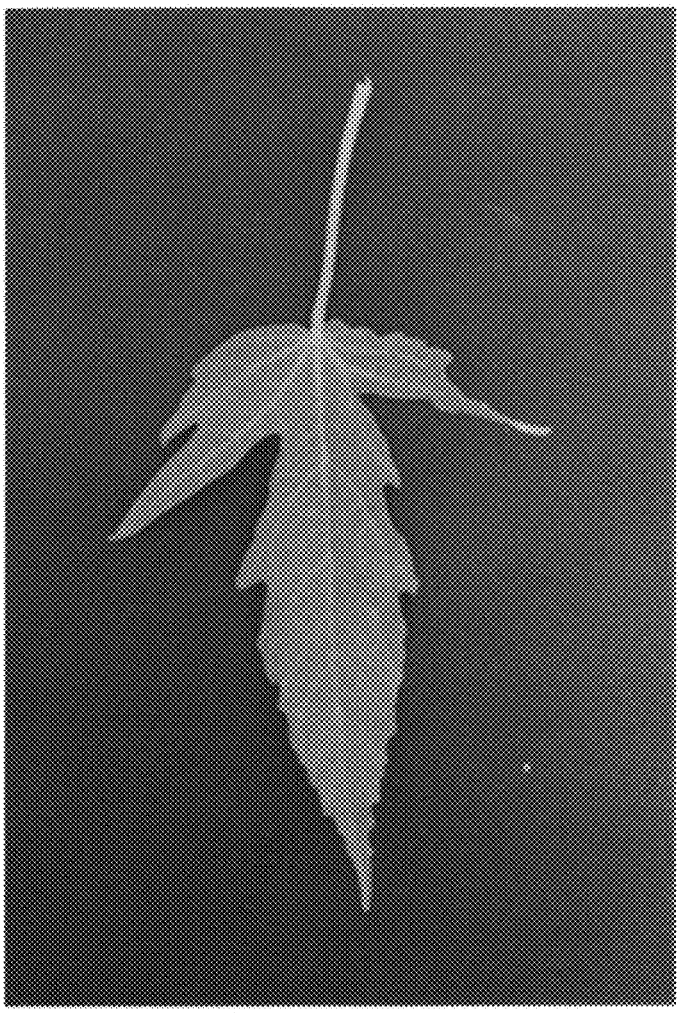
FIG. 4—Shows a '15734-1 GR' leaf.

The following detailed description sets forth the distinctive characteristics of '15734-1 GR'. The detailed description was obtained using two-year-old plants grown in loamy sand, open-field, full sun trials at a nursery near Vernon, Tex., during which the plants were supplemented with fertilizer and water as needed. These plants are natural habit and were not treated with plant growth regulators and they were not pinched at any time in the growth year. '15734-1 GR' has not been observed under all possible environments, and certain characteristics may vary slightly under different environmental conditions. Color references are to The Royal Horticultural Society Colour Chart of The Royal Horticultural Society of London (R.H.S.), 2001 ($4^{th}$ edition).

Propagation:

*Method*.—Stem cuttings.

*Time to initiate roots from stem cuttings after treating cuttings with a commercial rooting hormone*.—About 2 weeks under misting and at an air temperature of 85° C.

*Rooting habit*.—Normal, branching, fleshy, and developing a thick diameter (to about 2.5 cm).

*Root color*.—Pale yellow (between RHS 161D and RHS 162D), depending on soil type.

*Crop time* (*under normal summer growing conditions and when grown in a* 4 *l container from a rooted cutting*).—8 to 10 weeks to flower with very good plant vigor.

Plant:

*Plant shape and habit*.—Hardy herbaceous perennial with 8 to 10 thick upright and heavily branched main stems producing an upright spreading mound about 100.0 cm tall and 95.0 cm wide, which is widest about 50 cm above the soil line.

*Primary branches*.—8 to 16 per main stem that protrude at about a 45° angle from horizontal.

*Lateral branches*.—On the middle half of the primary stems.

*Lateral branch size*.—Between 15 cm and 30 cm long (shorter at the upper nodes) and with an average diameter of 8.0 mm at their base.

*Flower location*.—Upper ⅓ of the plant beginning at axillary nodes while still developing at the apex.

*Stem*.—Rounded, glabrous, glaucous; averages about 100.0 cm tall and 3.5 cm diameter at their base.

*Stem color*.—Between brilliant yellowish green (RHS 134C) and strong yellowish green (RHS 135C).

*Internode*.—About 18 nodes per stem below flower and about 32 total, average internode length is about 4.5 cm of unpinched plant, but varies between 2.0 to 6.0 cm and are widest in middle portion of stem.

Foliage:

*Shape*.—Hastate, trilobed with slightly indented margins.

*Texture*.—Adaxial and abaxial matte.

*Leaf blade size*.—To about 20.0 cm long and 10.0 cm wide, larger proximally and becoming smaller in distal portion of stem.

*Foliage color*.—Adaxial and abaxial strong yellowish green (RHS 135C).

*Veins*.—Palmate; adaxial and abaxial veins moderate yellowish green (RHS 139D).

*Petiole size* (*average*).—9.0 cm long and 5.0 mm wide.

*Petiole color*.—Between moderate yellow (RHS 163C) and light yellow (RHS 163D).

Flowers:

*Buds*.—One day prior to opening about 5.0 cm long and 2.5 cm in diameter, pointed apex and bluntly rounded base, unopened petals wrinkled at veins; and, prior to showing petals, about 3.4 cm long and 2.5 cm in diameter, ovoid with acute apex.

*Bud color*.—Exposed petal strong reddish purple (between RHS 72B to RHS 72C toward apex), with vein tinting of between strong purplish red (RHS 72A) and strong reddish purple (RHS 72B); and, prior to showing petals, strong reddish purple (RHS 72C).

*Epicalyx*.—Entire, smooth, puberulent both surfaces, linear with sharply acute apex and attenuate base, curved around sepals; typically 8 to 12 per flower; about 2.5 cm long tapering to base of about 3.0 mm wide.

*Epicalyx color*.—Adaxial and abaxial strong yellowish green (RHS 135C).

*Sepals*.—5, proximal half connate forming campanulate star-shaped calyx; acute apex; margin entire, edentate; puberulent abaxial glabrous adaxial; individually about 3.5 cm long and about 2.5 cm wide at fusion point. From the upper side of the flower, sepals visible as a star shape in the center of the flower.

*Sepal color*.—Abaxial and adaxial color strong yellowish green (RHS 135C). Flowers: Solitary, about 20 to 30 per main stem without pinching; primarily outwardly facing; average 20 cm across, larger in early part of flowering season; persist for one to two days, depending on temperature; effective for at least 14 weeks beginning early July and lasting into October (north Texas), no detectable fragrance.

*Petals*.—5; glabrous, slightly lustrous in the center and dull both front and back toward middle and perimeter, adnate to the androecium to form a column, slightly imbricate to about 10% overlapping at widest part (petals about 20% overlapping the next petal to either side). Veins: Palmately veined, primary and secondary veins impressed on front and ribbed on back; veins do not extend from the eye zone. Shape: Rounded. Margins: Entire, edentate. Apex: Rounded. Base: Short claw-like. Surface: Adaxial and abaxial glabrous, ribbed. Size (average): About 10.0 cm long and 10.0 cm wide at widest portion (largest in earlier part of flowering season); center dark eye about 4.0 cm diameter. Color: Adaxial and abaxial near strong reddish purple (RHS 72C), center eye between dark red (RHS 59A) and deep purplish red (RHS 59B).

*Gynoecium*.—Style: Enclosed in column about 7.5 cm long and 0.5 cm wide at base; column color vivid purplish red (RHS 61C); style protruding from column and split in distal 10.0 mm portion into typically 5 branches, branch diameter 2.0 mm; branch color nearest strong purplish red (RHS 60B). Stigma: Typically 5; globose, puberulose, about 3.0 mm in diameter; color nearest strong purplish red (RHS 60B). Ovary: Superior, about 6.5 mm across at base and 6.0 mm tall; acute apex.

*Androecium*.—Filaments: Numerous, about 160; less than 1.0 mm in diameter and about 5.0 mm long; attached along nearly the entire length of column; color nearest pale purplish pink (RHS 62D). Anthers: Reniform; about 2 mm long and 1 mm wide; nearest light yellow (RHS 163D). Pollen: Numerous, globose, less than 0.1mm long; color light yellow (RHS 163D).

*Pedicel*.—Rounded in cross section, finely puberulent; length from base of sepal to abscission point average 1.5 cm long and 4.0 mm wide, longer on early flowers decreasing in later flowers; color brilliant yellowish green (RHS 135C).

*Peduncle*.—Rounded, puberulent, average about 6.0 cm long from abscission point to stem and 4.0 mm wide, slightly longer on earlier flowers.

*Peduncle color*.—Brilliant yellowish green (RHS 135C).

*Fruit*.—Few, loculicidal capsule; glabrous; globose, occasionally with abruptly acute apex; color between light yellowish brown (RHS 199C) and dark grayish yellow (RHS 199D) when mature.

*Seed*.—Minutely floccose, typically globose; about 3.0 mm in diameter; color between dark grayish reddish brown (RHS 200A) and moderate brown (RHS 200C).

Resistance: The plant grows best with plenty of moisture, but is able to tolerate some drought once established. Other pest and disease resistance beyond that of other hardy perennial *hibiscus* cultivars has not been observed. Hardiness at least from USDA Zone 4 through 9.

Commercial use: Suitable for potted plant culture, landscaping as a specimen or en masse, and especially suited for patios and confined spaces because of the compact habit.

What is claimed is:

1. A new and distinct *Hibiscus* hybrid (L.) plant named '15734-1 GR' as shown and described herein.

* * * * *